United States Patent [19]

Mueller et al.

[11] Patent Number: 5,280,047
[45] Date of Patent: Jan. 18, 1994

[54] 2-(4-SUBSTITUTED)PHENYLMETHYLENE DERIVATIVES AND METHODS OF USE

[75] Inventors: Richard A. Mueller, Glencoe; Richard A. Partis, Evanston, both of Ill.

[73] Assignee: G. D. Searle & Co., Chicago, Ill.

[21] Appl. No.: 42,214

[22] Filed: Apr. 2, 1993

Related U.S. Application Data

[63] Continuation of Ser. No. 793,034, Nov. 18, 1991, abandoned.

[51] Int. Cl.$^5$ .............................................. A61U 31/12
[52] U.S. Cl. ..................................................... 514/678
[58] Field of Search ........................................ 514/678

[56] References Cited

U.S. PATENT DOCUMENTS

| | | | |
|---|---|---|---|
| 3,799,936 | 3/1974 | Meyer et al. | 260/295.5 R |
| 3,905,987 | 9/1975 | Booher | 260/296 R |
| 3,925,395 | 12/1975 | Meyer et al. | 290/294.8 |
| 3,932,646 | 1/1976 | Meyer et al. | 424/266 |
| 3,946,026 | 3/1976 | Meyer et al. | 260/295.5 R |
| 3,962,269 | 6/1976 | Booher | 260/296 R |
| 4,414,213 | 11/1983 | Poindexter et al. | 424/248 |
| 4,649,157 | 3/1987 | Partis et al. | 514/545 |
| 4,755,512 | 7/1988 | Poindexter et al. | 514/252 |
| 4,769,375 | 9/1988 | Meyer et al. | 514/311 |

FOREIGN PATENT DOCUMENTS 0195097 3/1985
0142145 5/1985

OTHER PUBLICATIONS

P. F. Juby, et al., J. Med. Chem., 15(12):1297–1306 (1972).
A. L. Weis, et al., ISR. J. Chem., 27(1):105–10 (1986).
CA 109:128499f
J. A. Cabello, et al., J. Org. Chem., 51(10):1786–90 (1986).
J. A. Ciller, et al., Org. Prep. Proced. Int., 18(4):227–36 (1986).

*Primary Examiner*—S. J. Friedman
*Attorney, Agent, or Firm*—Roberta L. Hastreiter; Roger A. Williams

[57] ABSTRACT

The present invention relates to methods of using and pharmaceutical compositions containing compounds of Formula I:

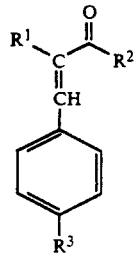

wherein $R^1$ is hydrogen, —$COR^4$ wherein $R^4$ is $C_1$–$C_4$ alkyl, or —$COOR^5$ wherein $R^5$ is $C_1$–$C_4$ alkyl; $R^2$ is $C_1$–$C_4$ alkyl, phenyl, or —$OR^6$ wherein $R^6$ is $C_1$–$C_4$ alkyl; and $R^3$ is $C_6$–$C_8$ alkyl, halogen, or $NO_2$; with the proviso that when $R^1$ is hydrogen, $R^2$ is $C_1$–$C_4$ alkyl; and a pharmaceutically acceptable carrier. Compounds of Formula I and pharmaceutical compositions containing them are inhibitors of 5-lipoxygenase and are useful in the treatment of conditions mediated by leukotrienes such as inflammation, allergy, hypersensitivity reactions, and proliferative skin diseases such as psoriasis.

14 Claims, No Drawings

2-(4-SUBSTITUTED)PHENYLMETHYLENE DERIVATIVES AND METHODS OF USE

This is a continuation of application Ser. No. 07/793,034, filed Nov. 18, 1991, now abandoned.

BACKGROUND OF THE INVENTION (a) Field of the Invention

This invention relates to pharmaceutical compositions containing a class of 2-(4-substituted)phenylmethylene derivatives useful as inhibitors of 5-lipoxygenase, an enzyme which plays an important role in leukotriene biosynthesis. This invention also relates to the use of 5-phenyl-1,3-dioxoalkenyl compounds as inhibitors of 5-lipoxygenase. By inhibiting 5-lipoxygenase and thus leukotriene biosynthesis, the compounds of this invention are useful in preventing or alleviating conditions associated with leukotrienes, such as allergic reactions, inflammatory conditions, immediate hypersensitivity reactions, asthma, and certain proliferative skin disorders such as psoriasis.

Arachidonic acid is converted enzymatically to various biologically active products, such as prostaglandins, thromboxanes, various hydroxyeicosatetraenoic and hydroperoxyeicosatetraenoic acids, and leukotrienes. The leukotrienes, products of the 5-lipoxygenase pathway, are implicated in allergic reactions, particularly asthma, see M. Griffin et al., *N. Engl. J. Med.*, 308, 436–439 (1983); inflammatory conditions; and skin diseases such as psoriasis. One leukotriene, $LTD_4$, is the major active constituent of slow reacting substance of anaphylaxis (SRS-A), a potent bronchoconstrictor that is released during allergic reactions. See R. A. Lewis and K. F. Austen, *Nature*, 293, 103–108 (1981). When administered to humans and guinea pigs, $LTD_4$ causes bronchoconstriction by two mechanisms: 1) directly by stimulating smooth muscle; and 2) indirectly through release of thromboxane $A_2$, which causes contraction of respiratory smooth muscle. Because antihistamines are ineffective in the management of asthma, SRS-A is believed to be a mediator of the bronchoconstriction occurring during an allergic attack. $LTD_4$ may also be involved in other inflammatory conditions such as rheumatoid arthritis. Another leukotriene, $LTC_4$, is also a very potent bronchoconstrictor. A third leukotriene, $LTB_4$, is associated with leukocyte chemotaxis, a phenomenon in which leukocytes migrate from the blood to an inflammatory site in response to chemical or biological stimuli, and may be involved in both acute and chronic inflammation. $LTB_4$ also appears to be associated with rheumatoid spondylitis and gout. Thus, the 5-lipoxygenase inhibitors of this invention, by inhibiting the production of leukotrienes, may prevent or alleviate the allergic, inflammatory, or hypersensitivity conditions associated with leukotrienes.

Non-steroidal antiinflammatory agents, such as aspirin, indomethacin, ibuprofen, and the like, inhibit prostaglandin biosynthesis by blocking the cyclooxygenase pathway of arachidonic acid metabolism. As a consequence, leukotriene levels may increase as arachidonic acid is metabolized along the 5-lipoxygenase pathway, producing allergic reactions. Administration of 5-lipoxygenase inhibitors of this invention may be effective in reducing undesirable side effects associated with non-steroidal antiinflammatory agents when administered separately or in combination.

See (1) P. Sirois, "Pharmacology of Leukotrienes" in *Advances in Lipid Research*, 21, 79–101 (1985); (2) M. K. Bach, "Inhibitors of Leukotriene Synthesis and Action" in *The Leukotrienes: Chemistry and Biology*, L. W. Chakrin and D. M. Bailey, eds., pp. 163–194 (Orlando: Academic Press, 1984); (3) M. K. Bach, *Bioch. pharmacol.*, 33, 515–521 (1984); (4) C. W. Lee et al., "Human Biology and Immunoreactivity of Leukotrienes" in *Advances in Inflammation Research*, 6, 219–225 (1984); (5) P. Sharon and W. F. Stenson, *Gastroenterology*, 84, 454–460 (1984); (6) E. L. Becker, *Trends Pharmacol. Sci.*, 4, 223–225 (1983); (7) Editorial, "Leukotrienes and Other Lipoxygenase Products in the Pathenogenesis and Therapy of Psoriasis and Dermatoses" in *Arch. Dermatol.*, 119, 541–547 (1983); (8) B. Samuelsson, *Science*, 220, 568–575 (1983); (9) R. A. Lewis et al., *Int. J. Immunopharmac.*, 4, 85–90 (1982); (10) M. W. Musch et al., *Science*, 217, 1255–1256 (1982).

Unlike earlier therapeutic agents that treat symptoms rather than causes, the compounds of this invention and the pharmaceutical compositions thereof block the formation of causative mediators of allergic and inflammatory conditions and are therefore useful in the treatment of allergic reactions, inflammation, and other conditions associated with leukotrienes.

(b) Background Information

European Patent Applications EP 0195097 and EP 0142145 disclose compounds of the formula

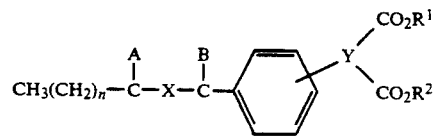

or a salt thereof,
in which Y is a group

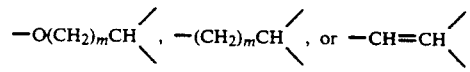

where m is an integer of from 1 to 5
n is an integer of from 4 to 12
each of $R^1$ and $R^2$, which may be the same or different, represents hydrogen or $C_{1-6}$ alkyl
X represents a double or triple bond, and each of
A and B represents hydrogen when X is a double bond, or both A and B are absent when X is a triple bond.

These compound are arachidonic acid analogues which are said to be useful in treating allergic diseases. These compounds differ structurally from the compounds of the present invention since they always have unsaturation in the hydrocarbon chain attached to the phenyl.

Some 2-(4-substituted)phenylmethylene compounds have been used as intermediates in the synthesis of other compounds.

J. MED. CHEM., 15(12):1297–1306 (1972) generically discloses intermediates of the formula

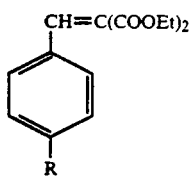

wherein R =H, alkyl, cycloalkyl which are used to make indan-1-carboxylic acids of the formula

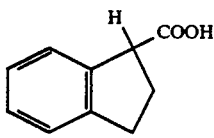

The indan-1-carboxylic acids are said to have antiinflammatory activity. Intermediates in which R is isopropyl, isobutyl, cyclopentyl, cyclohexyl, and cycloheptyl are specifically disclosed in Table II on page 1296. No biological activity is disclosed for the intermediates.

U.S. Pat. No. 3,925,395 generically discloses intermediates of the formula

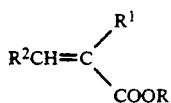

wherein $R^2$ is phenyl, unsubstituted or substituted by 1 to 3 of the same or different substituents selected from the group consisting of alkyl, especially lower alkyl, alkoxy, especially lower alkoxy, halogen, nitro. cyano, trifluoromethyl, carbalkoxy, especially carb/lower alkoxy and $SO_3$-alkyl, especially lower alkyl. These intermediates are used to make 4-aryl-6-amino-3,4-dihydro-pyrid-2-one-3,5-dicarboxylic acid esters which are said to be useful as coronary agents and as anti-hypertensive agents. No biological activity is disclosed for the intermediates.

U.S. Pat. No. 3,962,269 generically discloses intermediates of the formula $$ArCH=C(CO_2C_2H_5)_2$$

wherein Ar is phenyl, halophenyl, hydroxyphenyl, methoxyphenyl, methylphenyl, trifluoromethylphenyl, or 3-pyridyl. Intermediates of the formula

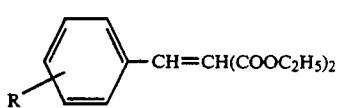

wherein R is 2-methyl, 3-methyl, 3-methoxy, 4-methoxy, 2-chloro, 3-chloro, 4-chloro, 2,4-dichloro, 4-fluoro, or 4-$\phi CH_2O$ are disclosed (See Table 2 at columns 13 and 14). No biological activity is given for these intermediates. They are used to make 2-substituted-1,3-propanediols which are also intermediates.

U.S. Pat. No. 3,799,936 and its divisional, U.S. Pat. No. 3,932,646 generically disclose intermediates of the formula

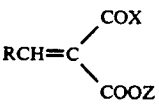

wherein R is phenyl, unsubstituted or substituted by up to three substituents selected from the group consisting of lower alkyl, lower alkoxy, halogeno, trifluoromethyl, or carbo-(lower alkoxy). These intermediates are used to make unsymmetrical esters of 1,4-dihydropyridine 3,5-dicarboxylates which are cardiovascular agents. No biological activity is disclosed for the intermediates.

U.S. Pat. No. 4,769,375 discloses benzylidene intermediates of the formula

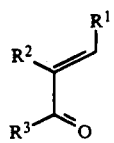

in which $R^1$ is phenyl which may be substituted with $C_1$-$C_4$-alkyl, F, Cl and $NO_2$; $R_2$ can be H or —$COR^5$, wherein $R^5$ is $C_1$-$C_4$ alkyl or —$OR^6$, wherein $R^6$ is $C_1$-$C_6$ alkyl; $R^3$ can be phenyl or $C_1$-$C_4$ alkyl. These benzilidene derivatives are used to prepare circulation-active 1,4-dihydropyridine derivatives. No biological activity is disclosed for the derivatives. No compounds in which $R^1$ is $C_1$-$C_4$-alkylphenyl are exemplified. No p-chlorophenyl or p-nitrophenyl compounds are exemplified.

U.S. Pat. No. 3,946,026 generically discloses dicarbonyl intermediates of the formula

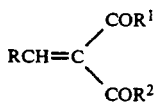

wherein R can be phenyl which can be substituted with lower alkyl, halogen or nitro; $R^1$ can be H, lower alkyl, phenyl, or pyridyl; and $R^2$ can be lower alkyl. These intermediates are used to make 2-amino-1,4-dihydropyridine derivatives which are said to be useful as antihypertensive agents and coronary vessel dilators. No biological activity is disclosed for the dicarbonyl intermediates.

U.S. Pat. No. 4,755,512 discloses intermediates of the formula

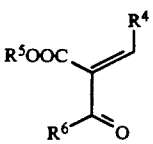

wherein $R^4$ can be cycloalkyl, aryl including phenyl, or hetaryl, which can be substituted with lower alkyl, lower alkoxy, cyano, halogen, hydroxyl, nitro, trifluoromethyl, etc., $R^5$ can be lower alkyl, $R^6$ can be lower alkyl, alkanol, alkoxyalkyl, or alkylaminoalkyl. Specifically disclosed are compounds of the formula wherein $R^4$=p-nitrophenyl, $R^5$=ethyl; $R^4$=o-chlorophenyl, $R^5$=ethyl; $R^4$=m-methylphenyl, $R^5$=ethyl; and $R^4$=phenyl, $R^5$=ethyl (See Table 2 at Columns 15-16).

These intermediates are used to make dihydropyridinyl-dicarboxylate amides and esters incorporating arylpiperazinyl moieties which are said to be useful as calcium and alphaadrenergic blockers and to have antihypertensive, antiischemic, and platelet function inhibiting actions. No biological activity is disclosed for the intermediates.

U.S. Pat. No. 4,414,213 discloses intermediates of the formula

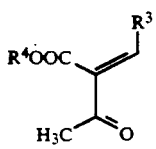

wherein $R^3$ can be phenyl substituted with acetamino, $C_1$-$C_4$ alkyl, $C_1$-$C_4$ alkoxy, cyano, halogen, hydroxyl, nitro, etc., and $R^4$ can be lower alkyl or alkoxyalkyl. Specifically disclosed are compounds in which $R^4$ is ethyl and $R^3$ is phenyl, p-nitrophenyl, m-chlorophenyl, and o-chlorophenyl (See Table 2 at Columns 8-9). These intermediates are used to make dihydropyridyl cyclicinidate esters which are said to demonstrate blockage of calcium ion flux and vasodilation activities. No biological activity is disclosed for the intermediates.

Weis, A. L, et al., ISR. J. CHEM., 27(1):105-10 (1986) discloses intermediates of the formula

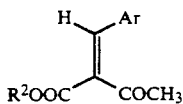

wherein Ar is phenyl and $R^2$ is methyl or ethyl; Ar is o-nitrophenyl and $R^2$ is methyl or ethyl; and Ar is m-nitrophenyl or p-nitrophenyl and $R^2$ is ethyl. The intermediates are used to make 4-aryl-1,4-dihydropyrimidine-5-carboxylate calcium antagonists. No biological activity is disclosed for the intermediates.

U.S. Pat. No. 3,905,987 discloses intermediates of the formula $$ArCH=C(CO_2C_2H_5)_2$$

wherein Ar can be phenyl, halophenyl, hydroxyphenyl, methoxyphenyl, methylphenyl, trifluoromethylphenyl, or 3-pyridyl (See Table 2 at Columns 14-15). These intermediates are used to make m-dioxane-5-methylamine analgesics. No biological activity is disclosed for the intermediates.

CA 109:128499f discloses benzilideneacetone intermediates of the formula $RC_6H_4CH:CHCOMe$ (R=4-$NO_2$, 4-Cl) used in a condensation reaction with arylamines. No biological activity is disclosed for the benzilideneacetone intermediates.

J. A. Cabello, et al., J. ORG. CHEM., 51(10):1786-90 (1986) discloses regioselective 1,4-hydrogenation of benzilidene ketone intermediates of the formula $XC_6H_4CH=CHCOR$. Specifically disclosed are compounds in which X,R=Me; X=Me, R=Ph (See Table II on page 1788). No biological activity is given for the benzilidene ketones.

J. A. Ciller, et al., ORG. PREP. PROCED. INT., 18(4):227-36 (1986) discloses intermediates of the formula

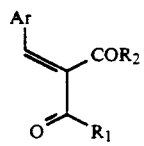

wherein Ar=p-$CH_3C_6H_4$, p-$ClC_6H_4$; $R_1$=$CH_3$ or $C_6H_5$, $R_2$=$CH_3$ or $C_6H_5$ (See Table 1 at page 230).

SUMMARY OF THE INVENTION

This invention relates to methods of using and pharmaceutical compositions comprising a compound of Formula I:

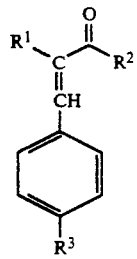

together with one or more non-toxic pharmaceutically acceptable carriers; wherein $R^1$ is:
a) hydrogen;
b)

wherein $R^4$ is $C_1$-$C_4$ alkyl; or
c)

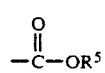

wherein $R^5$ is $C_1$-$C_4$ alkyl;
$R^2$ is:
a) $C_1$-$C_4$ alkyl;
b) phenyl; or
c) —$OR^6$ wherein $R^6$ is $C_1$-$C_4$ alkyl; and
$R^3$ is:
a) $C_6$-$C_8$ alkyl;
b) halogen; or
c) $NO_2$;
with the proviso that when $R^1$ is hydrogen, $R^2$ is $C_1$-$C_4$ alkyl.

The compounds of Formula I and pharmaceutical compositions containing a compound of Formula I are useful in inhibiting 5-lipoxygenase for treating inflammation, allergy, asthma, hypersensitivity reactions and proliferative skin diseases such as psoriasis.

This invention also relates to the use of the compounds of Formula I to inhibit 5-lipoxygenase and in the treatment of conditions associated with leukotrienes such as inflammation, allergy, asthma, hypersensitivity reactions, and proliferative skin diseases such as psoriasis.

Also included in the present invention are compounds of the formula

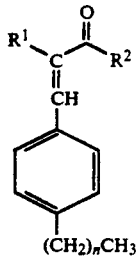

wherein
R¹ is:
a) hydrogen
b)

wherein R⁴ is $C_1$-$C_4$ alkyl;
c)

wherein R⁵ is $C_1$-$C_4$ alkyl;
R² is:
a) $C_1$-$C_4$ alkyl;
b) phenyl; or
c) OR⁶ wherein R⁶ is $C_1$-$C_4$ alkyl; and
n is an integer from 5 to 7; with the proviso that when R¹ is hydrogen, R² is $C_1$-$C_4$ alkyl.

The term "$C_1$-$C_4$ alkyl" refers to straight or branched chain alkyl groups having from 1 to 4 carbon atoms, also referred to as lower alkyl. Examples of $C_1$-$C_4$ alkyl are methyl, ethyl, propyl, butyl, isopropyl, isobutyl, t-butyl, and the isomeric forms thereof.

Examples of halogen are fluorine, chlorine, bromine, and iodine.

Although the structure shown for Formula I indicates one tautomeric form, it is understood that this representation is for convenience only and that the scope of this invention includes as equivalents all tautomeric keto and enol forms of the compounds of this invention as well as all isomeric forms of the compound of formula I including, for example, E, Z, cis, and trans isomers of compounds of Formula I.

DETAILED DESCRIPTION OF THE INVENTION

Biological Evaluation

The compounds of the invention are evaluated with respect to 5-lipoxygenase inhibition according to the following assay procedure.

Inhibition of 5-lipoxygenase, in vitro : anti-inflammatory, anti-allergy activities.

The 100,000 x g supernatant fraction of Rat Basophilic Leukemia Cell Homogenate (RBL-1) serves as a 5-lipoxygenase enzyme source. The enzyme is incubated with [1-$^{14}$C)-arachidonic acid and Ca++ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to determine the $IC_{50}$ value (inhibitory concentration to inhibit 50%).

The results with respect to certain compounds of the present invention are set forth in Table 1 below. When more than one result is listed, this indicates the results from additional tests.

TABLE 1

| Compound Example No. | 5-Lipoxygenase Inhibition $IC_{50}$ (μM) |
|---|---|
| 1A | 3, 7.9, 15 |
| 1B | 7.6, 5.9 |
| 2 | 18 |
| 3C | 5.9, 14 |
| 3D | 42% inhibition at 100 μM |
| 4 | 45.6% inhibition at 100 μM |
| 5 | 4.4 |
| 6E | 47 |
| 6F | 56 |
| 7G | 74 |
| 7H | 78 |
| 8 | 100 |
| 9 | 100 |
| 10 | 100 |

By virtue of their activity as inhibitors of 5-lipoxygenase, the compounds of Formula I are useful in treating conditions associated with leukotrienes, such as allergic reactions, particularly asthma; inflammatory conditions; and proliferative skin conditions such as psoriasis. A physician or veterinarian of ordinary skill can readily determine whether a subject exhibits the condition. The preferred utility relates to treatment of allergic reactions. Regardless of the route of administration selected, the compounds of the present invention are formulated into pharmaceutically acceptable dosage forms by conventional methods known to those skilled in the art.

The compounds can be administered in such oral dosage forms as tablets, capsules, pills, powders, granules, elixirs, or syrups. The compounds may also be administered intravascularly, intraperitoneally, subcutaneously, intramuscularly, topically, or transdermally, using forms known to the pharmaceutical art. In general, the preferred form of administration is oral. For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol, and the like, or various combinations thereof; for oral administration in liquid form, the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, active drug components may be combined with a suitable carrier such as water, saline, aqueous dextrose, and the like.

By whatever route of administration selected, an effective but non-toxic quantity of the compound is employed in treatment. The dosage regimen for preventing or treating leukotriene-associated conditions with the compounds of this invention is selected in accordance with a variety of factors, including the type, age, weight, sex, and medical condition of the patient; the severity of the condition; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention are ordinarily in the range of about 0.1 mg/kg per day up to about 100 mg/kg per day, preferably in the range of about 0.5 to 50 mg/kg per day.

The compounds of the invention can be prepared from readily available starting materials using the processes shown in Scheme 1 and Scheme 2.

In the process shown in Scheme 1, a benzaldehyde (III) is reacted with a ketone or ester of Formula (IV) in a base to give the phenylmethylene derivatives (V) and (VI).

In the process shown in Scheme 2, a benzaldehyde (III) is heated with a triphenylphosporanylidinealkanone (VIII) in toluene to give the produce (IX).

The definitions of $R_1$, $R_2$, and $R_3$ in Schemes 1 and 2 are the same as for $R^1$, $R^2$ and $R^3$ in Formula I.

Scheme 1

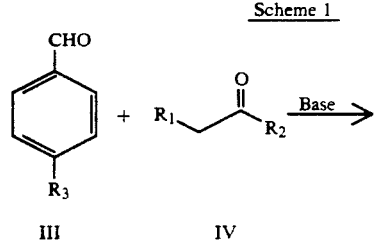

III   IV

-continued

Scheme 1

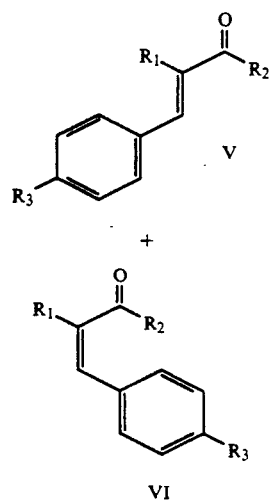

Scheme 2

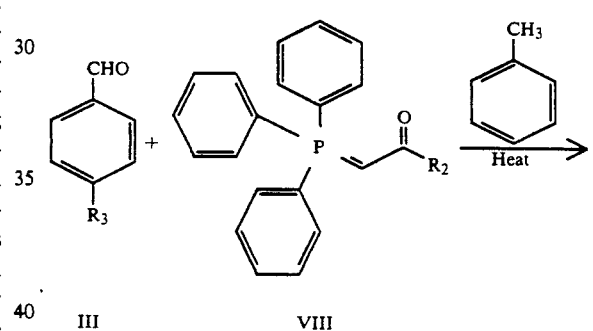

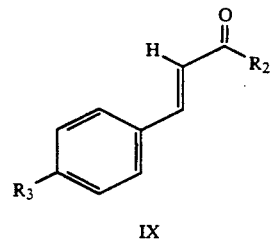

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

EXAMPLE 1

Product 1A (E): Ethyl 2E-[(4-hexylphenyl)methylene]-3-oxobutanoate

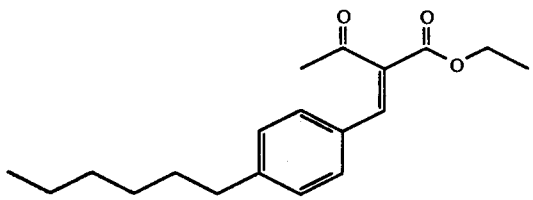

Product 1B (Z): Ethyl 2Z-[(4-hexylphenyl)methylene]-3-oxobutanoate

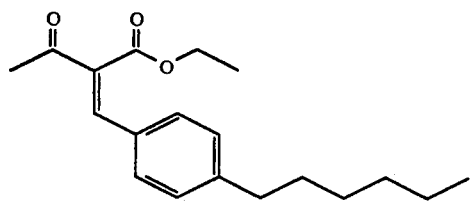

Ethyl acetoacetate (3.9g, 0.03 moles), parahexylbenzaldehyde (3.8g, 0.02 moles) and piperidine (3 drops) were stirred at room temperature for 20 hrs. and then stirred for 4 days at 70° C. Products A and B were separated and purified by silica gel chromatography. Structure assignments were supported by NMR, infrared and uv spectra and elemental analysis (302.4).

Product 1A
Analysis calcd. for $C_{19}H_{26}O_3$: C, 75.46; H, 8.67. Found: C, 75.73; H, 8.90.

Product 1B
Analysis calcd. for $C_{19}H_{26}O_3$: C, 75.46; H, 8.67. Found: C, 75.76; H, 8.82.

EXAMPLE 2

2Z-[(4-hexylphenyl)methylene]-1-phenyl-1,3-butanedione

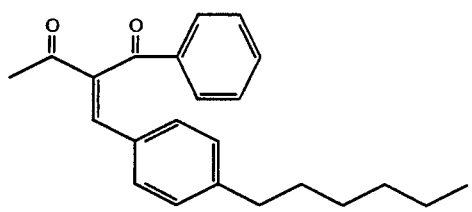

Benzoylacetone (0.65g, 0.004 moles), parahexylbenzaldehyde (0.76g, 0.004 moles) and piperidine (3 drops) were stirred in ethyl ether (10ml) for 20 hrs. An additional 200mg benzoylacetone was added and the solution stirred for 48 hrs. The solution was concentrated to an oil with a gentle stream of Nitrogen. The product was purified by silica gel chromatography. The structure assignment was supported by NMR, infrared and uv spectra and elemental analysis (334.5).

Analysis calcd. for $C_{23}H_{26}O_2$: C, 82.60; H, 7.84. Found: C, 82.60; H, 8.01.

EXAMPLE 3

Product C: Ethyl 2E-[(4-octylphenyl)methylene]-3-oxobutanoate

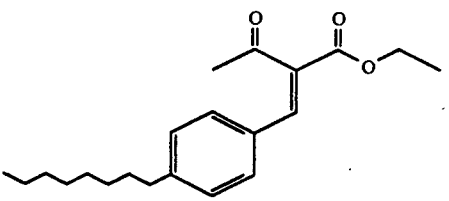

Product D: Ethyl 2Z-[(4-octylphenyl)methylene]-3-oxobutanoate

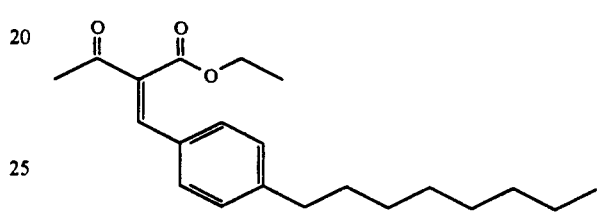

Ethyl acetoacetate (11.8g, 0.092 moles), paraoctylbenzaldehyde (10.0 g, 0.046 moles) and piperidine (1.5ml) were stirred for 48 hrs. at room temperature. Ethyl acetate (50ml) was added and the solution was added to water (100ml). The layers were separated and the organic layer dried over anhydrous sodium sulfate, filtered and concentrated to an oily solid. The title products were separated and purified by silica gel chromatography. The structure assignments were supported by NMR, infrared spectra and elemental analysis (330.5)

Product C
Analysis calcd. for $C_{21}H_{30}O_3$: C, 76.33; H, 9.15. Found: C, 76.72; H, 9.48.

Product D
Analysis calcd. for $C_{21}H_{30}O_3$: C, 76.33; H, 9.15. Found: C, 76.59; H, 9.31.

EXAMPLE 4

Diethyl 2-[(4-octylphenyl)methylene]propanedioate

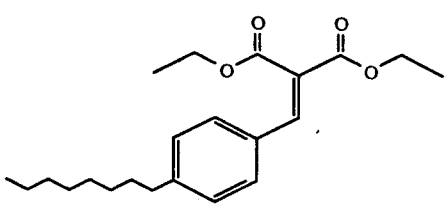

Diethyl malonate (1.76g, 0.011 moles), paraoctylbenzaldehyde (2.4g, 0.011 moles) and piperidine (5 drops) were heated to 98° C. for 2.5 hrs. and 45° C. for 16 hrs. The solution was heated to 100° C. for 64 hrs. The title compound was purified by silica gel chromatography. The structure assignment was supported by NMR, infrared and uv spectra and elemental analysis (360.5).

Analysis calcd. for $C_{22}H_{32}O_4$: C, 73.30; H, 8.95. Found: C, 73.48; H, 9.14.

EXAMPLE 5

3-[(4-octylphenyl)methylene]-2,4-pentanedione

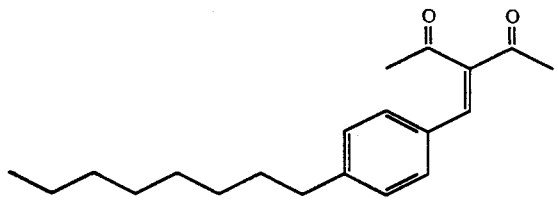

Piperidine (5 drops) was added to a solution of pentanedione (1.01 g 0.01 moles) and paraoctylbenzaldehyde (2.18g, 0.01 moles) at 0° C. The solution was stirred at 0° C for 6 hrs and then at room temperature for 4 days. The title compound was purified by silica gel chromatography. The structure assignment was supported by NMR, infrared and uv spectra and elemental analysis (300.4).

Analysis calcd. for $C_{20}H_{28}O_2$: C, 79.96; H, 9.39. Found: C, 80.23; H, 9.45.

EXAMPLE 6

Product E: Ethyl 2E-[(4-chlorophenyl)methylene]-3-oxobutanoate

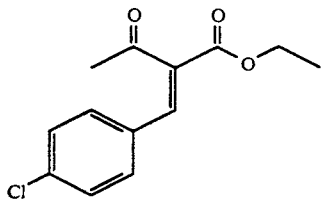

Product F: Ethyl 2Z-[(4-chlorophenyl)methylene]-3-oxobutanoate

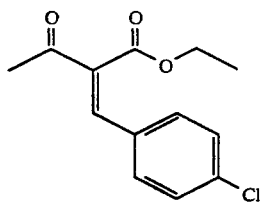

Piperidine (5 drops) was added to a solution of paraoctylbenzaldehyde (7.0g, 0.05 moles) and ethyl acetoacetate (6.5g, 0.05 moles) and stirred at room temperature for 3 days. The titled products were separated and purified by silica gel chromatography. The structure assignments were supported by NMR, infrared and uv spectra and elemental analysis (252.7).

Product E

Analysis calcd. for $C_{13}H_{13}ClO_3$: C, 61.79; H, 5.18; Cl, 14.03. Found: C, 61.94; H, 5.27; Cl, 14.08.

Product F (DSC ca. 87° C.)

Analysis calcd. for $C_{13}H_{13}ClO_3$: C, 61.79; H, 5.18; Cl, 14.03. Found: C, 61.82; H, 5.25; Cl, 13.73.

EXAMPLE 7

Product G: Ethyl 2E-[(4-nitrophenyl)methylene]-3-oxobutanoate

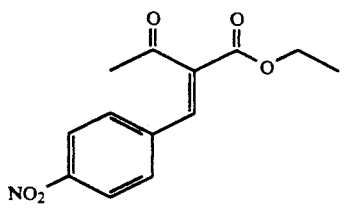

Product H: Ethyl 2Z-[(4-nitrophenyl)methylene]-3-oxobutanoate

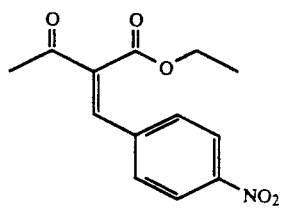

Piperidine (0.5ml) was added to a solution of paranitrobenzaldehyde (7.5g, 0.05 moles) and ethyl acetoacetate (6.5g, 0.05 moles) and stirred at room temperature for 48 hrs. Ethyl ether (50ml) was added and stirring continued for 7 days. After removal of the ethyl ether by rotary evaporator the titled products were separated and purified by silica gel chromatography. The structure assignments were supported by NMR, infrared and uv spectra and elemental analysis (263.2).

Product G (DSC ca. 93° C.)

Analysis calcd. for $C_{13}H_{13}NO_5$: C, 59.31; H, 4.98; N, 5.32. Found: C, 59.39; H, 4.69; N, 5.28.

Product H (DSC ca. 77° C.)

Analysis calcd. for $C_{13}H_{13}NO_5$: C, 59.31; H, 4.98; N, 5.32. Found: C, 59.33; H, 4.92; N, 5.37.

EXAMPLE 8

4-(4-octylphenyl)-3E-buten-2-one

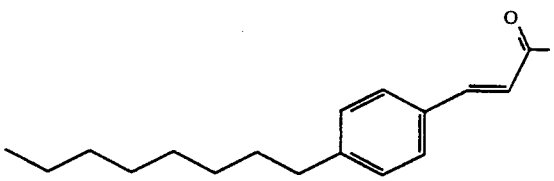

Triphenylphosporanylidene-2-propanone (2.9q, 0.0092 moles) and para-octylbenzaldehyde (2.0g, 0.0092 moles) in toluene (50ml) was heated to reflux for 2 hrs. and then stirred at room temperature for 64 hrs. The solution was poured into a solution of ethyl ether (100 ml) and hexane (100 ml). The white solid was removed by filtration and the filtrate concentrated by rotary evaporator to an oil. The title product was purified by silica gel chromatography. The structure assignment was supported by NMR, infrared spectra and elemental analysis (258.4).

Analysis calcd. for $C_{18}H_{26}O$: C, 83.67; H, 10.14. Found: C, 83.69; H, 10.44.

EXAMPLE 9

4-(4-hexylphenyl)-3E-buten-2-one

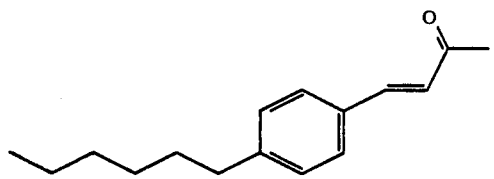

Following the method of Example 8 and substituting para-hexylbenzaldehyde for para-octylbenzaldehyde the title compound was obtained (230.35)

Analysis calcd. for $C_{16}H_{22}O$ : C, 83.43; H, 9.63. Found: C, 83.58; H, 9.81.

EXAMPLE 10

Diethyl 2-[(4-hexylphenyl)methylene]propanedioate

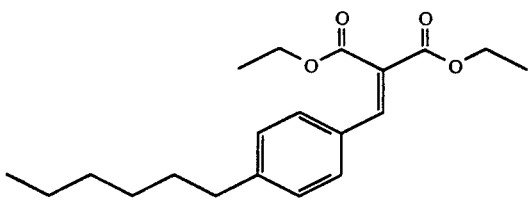

Diethyl malonate (1.68 g, 0.0105 mole), parahexylbenzaldehyde (2.0 g, 0.0105 mole) and piperidine (5 drops) were heated to 85° C for 20 hrs. and then at 100° C. for 5 hrs. The title compound was purified by silica gel chromatography. The structure assignment was supported by NMR, infrared and UV spectra and elemental analysis (332.4).

Analysis calcd. for $C_{20}H_{28}O_4$: C, 72.26; H, 8.49. Found: C, 72.03; H, 8.69.

What is claimed is:

1. A method of inhibiting 5-lipoxygenase in a mammal in need of such treatment which comprises administering to the mammal a therapeutically effective 5-lipoxygenase inhibiting amount of a compound of the formula

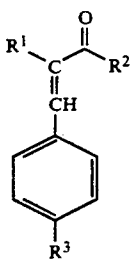

wherein
$R^1$ is:
a) hydrogen,
b)

wherein $R^4$ is $C_1$-$C_4$ alkyl, or
c)

wherein $R^5$ is $C_1$-$C_4$ alkyl;
$R^2$ is:
a) $C_1$-$C_4$ alkyl or
b) phenyl, and
$R^3$ is:
a) $C_6$-$C_8$ alkyl,
b) halogen, or
c) $NO_2$;
with the proviso that when $R^1$ is hydrogen, $R^2$ is $C_1$-$C_4$ alkyl.

2. A method according to claim 1 wherein $R^2$ is methyl, ethyl or phenyl; $R^3$ is hexyl, octyl, Cl, or $NO_2$; $R^4$ is methyl or ethyl, and $R^5$ is methyl or ethyl.

3. A method of treating inflammatory or allergic conditions in a mammal in need of such treatment which comprises administering to the mammal a therapeutically effective amount of a compound of the formula

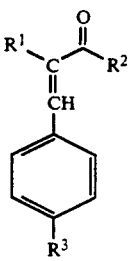

wherein
$R^1$ is:
a) hydrogen,
b)

wherein $R^4$ is $C_1$-$C_4$ alkyl, or
c)

wherein $R^5$ is $C_1$-$C_4$ alkyl;
$R^2$ is:
a) $C_1$-$C_4$ alkyl or
b) phenyl, and
$R^3$ is:
a) $C_6$-$C_8$ alkyl,
b) halogen, or
c) $NO_2$;
with the proviso that when $R^1$ is hydrogen, $R^2$ is $C_1$-$C_4$ alkyl.

4. A method according to claim 3 wherein $R^2$ is methyl, ethyl or phenyl; $R^3$ is hexyl, octyl, Cl, or $NO_2$; $R^4$ is methyl or ethyl, and $R^5$ is methyl or ethyl.

5. A method according to claim 3 of treating psoriasis in a mammal in need of such treatment which comprises administering to the mammal a therapeutically effective amount of a compound of the formula

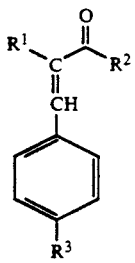

wherein
R¹ is:
  a) hydrogen;
  b)

wherein R⁴ is C₁-C₄ alkyl;
  c)

wherein R⁵ is C₁-C₄ alkyl;
R² is:
  a) C₁-C₄ alkyl or
  b) phenyl; and
R³ is:
  a) C₆-C₈ alkyl;
  b) halogen; or
  c) NO₂;
with the proviso that when R¹ is hydrogen, R² is C₁-C₄ alkyl.

6. A method according to claim 5 wherein R² is methyl, ethyl or phenyl; R³ is hexyl, octyl, Cl, or NO₂; R⁴ is methyl or ethyl, and R⁵ is methyl or ethyl.

7. A method according to claim 1 wherein said compound is selected from the group consisting of
2Z-[(4-hexylphenyl)methylene]-1-phenyl-1,3-butanedione;
3-[(4-octylphenyl)methylene]-2,4-pentanedione;
4-(4-octylphenyl)-3E-buten-2-one; and
4-(4-hexylphenyl)-3E-buten-2-one.

8. A method according to claim 3 wherein said compound is selected from the group consisting of
2Z-[(4-hexylphenyl)methylene]-1-phenyl-1,3-butanedione;
3-[(4-octylphenyl)methylene]-2,4-pentanedione;
4-(4-octylphenyl)-3E-buten-2-one; and
4-(4-hexylphenyl)-3E-buten-2-one.

9. A method according to claim 5 wherein said compound is selected from the group consisting of
2Z-[(4-hexylphenyl)methylene]-1-phenyl-1,3-butanedione;
3-[(4-octylphenyl)methylene]-2,4-pentanedione;
4-(4-octylphenyl)-3E-buten-2-one; and
4-(4-hexylphenyl)-3E-buten-2-one.

10. A pharmaceutical composition for use in inhibiting 5-lipoxygenase in a mammal in need of such treatment which comprises from 0.1 mg to 100 mg per unit dose in the form of a tablet, capsule, pill, powder, granule, elixir, or syrup of a compound of the formula

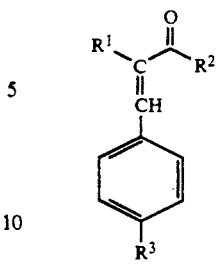

wherein
R¹ is:
  a) hydrogen;
  b)

wherein R⁴ is C₁-C₄ alkyl;
  c)

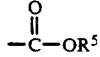

wherein R⁵ is C₁-C₄ alkyl;
R² is:
  a) C₁-C₄ alkyl or
  b) phenyl; and
R³ is:
  a) C₆-C₈ alkyl;
  b) halogen; or
  c) NO₂;
with the proviso that when R¹ is hydrogen, R² is C₁-C₄ alkyl; and a pharmaceutically acceptable carrier.

11. A pharmaceutical composition according to claim 10 wherein R² is methyl, ethyl or phenyl; R³ is hexyl, octyl, Cl, or NO₂; R⁴ is methyl or ethyl, and R⁵ is methyl or ethyl.

12. A pharmaceutical composition according to claim 10 wherein said compound is selected from the group consisting of
2Z-[(4-hexylphenyl)methylene]-1-phenyl-1,3-butanedione;
3-[(4-octylphenyl)methylene]-2,4-pentanedione;
4-(4-octylphenyl)-3E-buten-2-one; and
4-(4-hexylphenyl)-3E-buten-2-one.

13. A pharmaceutical composition for use in inhibiting 5-lipoxygenase in a mammal in need of such treatment which comprises from 0.1 mg to 100 mg per unit dose of a compound of the formula

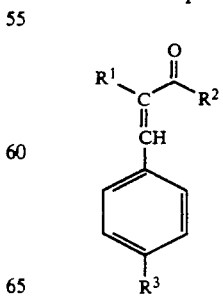

wherein
R¹ is:

a) hydrogen;
b)

wherein $R^4$ is $C_1$–$C_4$ alkyl;
c)

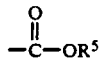

wherein $R^5$ is $C_1$–$C_4$ alkyl;
$R^2$ is:
a) $C_1$–$C_4$ alkyl or
b) phenyl; and $R^3$ is:
a) $C_6$–$C_8$ alkyl;
b) halogen; or
c) $NO_2$;

with the proviso that when $R^1$ is hydrogen, $R^2$ is $C_1$–$C_4$ alkyl; and a pharmaceutically acceptable carrier, in a pharmaceutically acceptable dosage form for intravascular, intraperitoneal, subcutaneous, intramuscular, or topical administration.

14. A pharmaceutical composition according to claim 13 wherein said compound is selected from the group consisting of
2Z-[(4-hexylphenyl)methylene-1-phenyl-1,3-butanedione;
3-[(4-octylphenyl)methylene]-2,4-pentanedione;
4-(4-octylphenyl)-3E-buten-2-one; and
4-(4-hexylphenyl)-3E-buten-2-one.

* * * * *

UNITED STATES PATENT AND TRADEMARK OFFICE
CERTIFICATE OF CORRECTION

PATENT NO. : 5,280,047
DATED : January 18, 1994
INVENTOR(S) : Mueller, et al.

It is certified that error appears in the above-identified patent and that said Letters Patent is hereby corrected as shown below:

Column 2, line 6, reading "pharmacol." should read -- Pharmacol. --.

Column 3, line 37, reading "nitro." should read -- nitro, --.

Column 4, line 60, reading "cycloalkyl," should read -- cycloaryl --.

Column 9, line 53, reading "produce (IX)." should read -- product (IX). --.

Column 12, line 38, reading "(330.5)" should read -- (330.5). --.

Column 14, line 56, reading "(2.9q, 0.0092" should read -- (2.9g, 0.0092 --.

Signed and Sealed this

Seventh Day of November, 1995

Attest:

BRUCE LEHMAN

Attesting Officer

Commissioner of Patents and Trademarks